(12) United States Patent
He et al.

(10) Patent No.: US 11,680,271 B2
(45) Date of Patent: Jun. 20, 2023

(54) CONSTRUCTION OF FULLY HUMAN ANTIBODY YEAST DISPLAY TECHNIQUE

(71) Applicant: ADLAI NORTYE BIOPHARMA CO., LTD., Hangzhou (CN)

(72) Inventors: Nanhai He, Hangzhou (CN); Dandan Chen, Hangzhou (CN); Yang Lu, Hangzhou (CN); Donghui Yang, Hangzhou (CN)

(73) Assignee: ADLAI NORTYE BIOPHARMA CO., LTD., Hangzhou (CN)

( * ) Notice: Subject to any disclaimer, the term of this patent is extended or adjusted under 35 U.S.C. 154(b) by 159 days.

(21) Appl. No.: 17/321,603

(22) Filed: May 17, 2021

(65) Prior Publication Data

US 2022/0135988 A1  May 5, 2022

(30) Foreign Application Priority Data

Nov. 5, 2020 (CN) .................. 202011222159.X (51) Int. Cl.
*C40B 40/08* (2006.01)
*C12N 15/81* (2006.01)
*C12N 15/10* (2006.01)

(52) U.S. Cl.
CPC ......... *C12N 15/81* (2013.01); *C12N 15/1037* (2013.01); *C40B 40/08* (2013.01); *C12N 2800/102* (2013.01)

(58) Field of Classification Search
None
See application file for complete search history.

(56) References Cited

U.S. PATENT DOCUMENTS

| | | | |
|---|---|---|---|
| 6,610,472 B1 | 8/2003 | Zhu et al. | |
| 10,011,829 B2 | 7/2018 | Fan | |
| 2003/0206909 A1 | 11/2003 | Hua et al. | |
| 2012/0294799 A1 | 11/2012 | Scholler et al. | |
| 2016/0304856 A1 | 10/2016 | Fan | |
| 2019/0119691 A1 | 4/2019 | Chatterjee et al. | |

FOREIGN PATENT DOCUMENTS

| | | |
|---|---|---|
| CA | 2462113 A1 | 4/2003 |
| CN | 111440816 A | 7/2020 |
| WO | 03066830 A2 | 8/2003 |
| WO | 2017175176 A1 | 10/2017 |
| WO | 2020177719 A1 | 9/2020 |

OTHER PUBLICATIONS

EP 21173078.3 Extended European Search Report dated Oct. 14, 2021.
China 2020116409589 Search Report dated Jul. 29, 2022.

*Primary Examiner* — Christian C Boesen
(74) *Attorney, Agent, or Firm* — Honigman LLP; Thomas A. Wootton, Esq.; Jonathan P. O'Brien (57) ABSTRACT

The present disclosure application relates to a construction method of a yeast display library (YSD), specifically to a construct for a yeast display library, an expression vector, a host cell and a construction method and use thereof. The yeast display library provided by the present application has high transformation efficiency and rich diversity.

16 Claims, 4 Drawing Sheets

Specification includes a Sequence Listing.

CONSTRUCTION OF FULLY HUMAN ANTIBODY YEAST DISPLAY TECHNIQUE

This application claims priority under 35 U.S.C. § 119, which claims the benefit of Paris Convention application CN202011222159X, filed Nov. 5, 2020. Priority is claimed to this application and the disclosure of this prior application is considered part of the disclosure of this application and to the extent allowed the entire contents of the aforementioned application is incorporated herein.

SEQUENCE LISTING

This application incorporates by reference in its entirety the Sequence Listing entitled "2021-04-28_262790-483476_ST25.txt" is 14,091 bytes in size and was created on Apr. 28, 2021, and filed electronically herewith.

FIELD OF THE INVENTION

The present application relates to the technical field of genetic engineering, specifically to a construct for a yeast display library, an expression vector, a host cell, and a construction method and a use thereof.

BACKGROUND OF THE INVENTION

At present, more commonly used antibody screening techniques include in vivo screening and in vitro screening, and in vitro screening technique is favored due to its simple and rapid characteristics. The in vitro screening technique is based on the construction of an antibody library, and the mature technique mainly includes phage display technique and yeast display technique. The phage display technique, as the earliest in vitro antibody screening technique, has been widely used in the development of antibody drugs, and a large number of marketed drugs have been approved for use. The principle for the phage display is that an antibody heavy chain variable region (VH) and a light chain variable region (VL) of B lymphocytes are amplified by a PCR (polymerase chain reaction) method, the amplified fragment is inserted into a phage vector, with an antibody molecule and a single-chain phage ghost protein being displayed on the surface of the phage in the form of a fusion protein, then the phage is transfected into a host cell for proliferation, and is released after maturation, and finally, a target antigen-specific monoclonal phage antibody is obtained by using an antigen screening method through the steps of affinity adsorption, elution, and amplification.

The phage display technique, as the first-generation in vitro antibody screening technique, has advantages over in-vivo antibody screening but has obvious disadvantages. Firstly, as phages grow and propagate in prokaryotic bacteria so that the expression and production of antibodies are in a completely different system, it is difficult to mimic the various post-translational modifications possessed by antibodies in mammals. However, these modifications are critical to the function of the antibody in some cases. Secondly, the loss of diversity in phage antibody libraries is likely to occur in the continuous amplification of bacteria. Since antibodies are continuously expressed in bacteria, some of which will affect the division and proliferation of bacteria, so this part of antibodies is easily lost during the continuous division and proliferation of bacteria. At the same time, not all antibody sequences are well expressed in phages, which also affects the diversity of antibody libraries. These disadvantages have also prompted scientists to continually search for better in vitro screening techniques for antibodies.

Yeast display technique is an in vitro antibody screening technique developed subsequently, which is considered to be better than phage display. The basic principle is that a foreign target protein gene (foreign protein) is fused with a specific vector gene sequence and then introduced into a yeast cell, the fusion protein containing a structure capable of anchoring on the cell wall of the yeast can be immobilized and expressed on the surface of the yeast cell after transcription and translation. The advantages are as follows: firstly, the yeast expression system not only has the characteristics of a prokaryotic bacterial expression system, such as simple operation, and rapid propagation, but also has the functions of processing and modifying proteins since the yeast expression system belongs to a eukaryotic system so that the expressed antibodies are closer to the real situation. Secondly, yeast individuals are much larger than bacteria, which allows the screening of yeast display techniques to be organically combined with flow cytometry. Using flow cytometry for screening has great advantages, not only the throughput and speed of screening are greatly improved, but also the affinity of antibodies can be tracked and estimated very intuitively, which greatly improves screening efficiency. Thirdly, many properties of the antibody may be set specifically by using flow cytometry for screening, such as binding or blocking antibodies, species selectivity, and specificity among different subtypes. Fourthly, the diversity of antibodies results in good fidelity in yeast systems. The experimental results show that the diversity of the antibody library remains unchanged even after more than 200 generations of yeast cultivation.

Yeast display technique has significant advantages over phage display technique but also has its disadvantages. For example, the current antibody library has a relatively low capacity, which has a greater impact on the diversity of antibodies. The relatively inefficient recombination between yeast expression plasmids and antibody fragments also limits the diversity of antibodies.

Therefore, there is a need in the art for a method of constructing a yeast display library with high transformation efficiency and rich diversity.

SUMMARY OF THE INVENTION

The present application provides a yeast display library with high transformation efficiency and rich diversity.

In a first aspect of the present invention, there is provided a construct including a promoter, a multiple cloning site region, a CH1 fragment of a human IgG heavy chain constant region, a linker sequence, a yeast surface localization sequence, and optionally a tag sequence.

In a specific embodiment, the construct includes the structure of Expression (I):

Expression (I):

5'-A-B-C-D-E-F-3'          (I); where,

A represents the promoter;
B represents the multiple cloning site region;
C represents the CH1 fragment of the human IgG heavy chain constant region;
D represents the linker sequence;
E represents the yeast surface positioning sequence; and
F represents none or the tag sequence.

In a specific embodiment, the promoter is selected from the group consisting of: yeast GAL1 promoter, yeast GAL10 promoter, and yeast GAL1/GAL10 bidirectional promoter.

In a specific embodiment, the linker sequence is a glycine- and serine-rich linker.

In a specific embodiment, the linker is selected from $(Gly_4Ser)_3$ and $(GlySer)_5$.

In a specific embodiment, the yeast surface localization sequence is selected from the group consisting of Aga1p polypeptide or fragment thereof, Aga2p polypeptide or fragment thereof, and Sag1p polypeptide or fragment thereof.

In a specific embodiment, the tag sequence is selected from the group consisting of c-Myc, V5, hexahistidine, glutathione-S-transferase, streptavidin, biotin, hemagglutinin, Flag tag, and E tag.

In a specific embodiment, the construct includes the nucleotide sequence shown in SEQ ID NO:1.

In a second aspect of the present invention, there is provided a use of the construct in the preparation of a recombinant vector.

In a specific embodiment, the recombinant vector may be replicated and expressed in bacterial and yeast host cells.

In a third aspect of the present invention, there is provided a recombinant vector including the construct.

In a specific embodiment, the construct includes the nucleotide sequence shown in SEQ ID NO:1.

In a specific embodiment, the vector is selected from the group consisting of plasmids, vectors, phages, cosmids, and viruses.

In a specific embodiment, the plasmid is a yeast plasmid.

In a specific embodiment, the yeast plasmid is selected from the group consisting of yeast integration plasmids, yeast replication plasmids, yeast replication plasmids incorporating centromere elements, yeast-free plasmids, and yeast linear plasmids.

In a specific embodiment, the recombinant vector includes the nucleotide sequence shown in SEQ ID NO:2.

In a fourth aspect of the present invention, there is provided a kit including the recombinant vector of the third aspect.

In a specific embodiment, the kit further includes one or more reagents selected from the group consisting of primers, endonucleases, and DNA ligases.

In a specific embodiment, the primers are used to amplify a target protein sequence.

In a specific embodiment, the primer includes the primers with the sequence shown in SEQ ID NO:3-SEQ ID NO:20.

In a specific embodiment, the recombinant vector includes the nucleotide sequence shown in SEQ ID NO:2.

In a specific embodiment, the kit is used to insert a target protein sequence into the recombinant vector.

In a fifth aspect of the present invention, there is provided a use of the kit of the fourth aspect in the preparation of an expression vector for a target protein.

In a sixth aspect of the present invention, there is provided an expression vector obtained by inserting a target protein sequence into the recombinant vector of the third aspect.

In a specific embodiment, the target protein sequence includes an antigen-binding sequence.

In a specific embodiment, the antigen-bindingantigen-binding sequence is selected from the group consisting of heavy chains, light chains, heavy chain-light chain dimers, Fab fragments, F(ab')2 fragments, Fv fragments, single chain Fv(scFv), and dAb.

In a specific embodiment, the antigen-binding sequence is a human antibody gene sequence.

In a specific embodiment, the human antibody gene sequence includes a human antibody gene heavy chain sequence, a human antibody gene light chain sequence, or a combination thereof.

In a specific embodiment, the human antibody gene light chain sequence is selected from the group consisting of human kappa light chain gene sequence and human lambda light chain gene sequence.

In a specific embodiment, the expression vector is prepared using the kit of the fourth aspect.

In a seventh aspect of the present invention, there is provided a use of the expression vector in the preparation of yeast display cells.

In an eighth aspect of the present invention, there is provided a cell construction method including:

a) inserting a target protein sequence into the vector V0 of the third aspect to obtain an expression vector V1; and b) introducing the expression vector V1 obtained in step a) into a host cell to obtain a recombinant host cell.

In a specific embodiment, where the vector V0 includes the nucleotide sequence shown in SEQ ID NO:2.

In a specific embodiment, the host cell is a yeast cell.

In a specific embodiment, the yeast cell is selected from the group consisting of: *Saccharomyces cerevisiae, Pichia pastoris*, and derivatives thereof.

In a specific embodiment, the target protein is expressed on the surface of the recombinant host cell obtained in step b).

In a ninth aspect of the present invention, there is provided a host cell including the expression vector of the third aspect.

In a specific embodiment, the host cell is constructed according to the method of the eighth aspect.

In a specific embodiment, the host cell expresses at least $10^2$, at least $10^3$, at least $10^4$, or at least $10^5$ target proteins.

In a specific embodiment, the target protein is an antibody or an antigen-binding protein.

In a specific embodiment, the antibody or antigen-binding protein is a human antibody or an antigen-binding protein.

In a specific embodiment, the host cell is a yeast cell expressing a fully human antibody or an antigen-binding protein.

In a specific embodiment, the yeast cell is a yeast display cell expressing a fully human antibody or an antigen-binding protein.

In a tenth aspect of the present invention, there is provided a host cell display library including at least two host cells of the ninth aspect.

In a specific embodiment, the host cell display library is a yeast cell display library.

In a specific embodiment, the host cell display library is used to provide an antibody display library.

In a specific embodiment, the host cell display library displays at least $10^2$, at least $10^4$, at least $10^6$, or at least $10^8$ fully human antibodies or antigen-binding proteins.

Other aspects and advantages of the present application will become readily apparent to those skilled in the art from the following detailed description. Only exemplary embodiments of the present application are shown and described in the following detailed description. As will be recognized by those skilled in the art, the contents of this application enable those skilled in the art to make modifications to the specific embodiments disclosed without departing from the spirit and scope of the present invention to which this application pertains. Accordingly, the drawings and description herein are to be regarded as illustrative, and not as restrictive.

BRIEF DESCRIPTION OF THE DRAWINGS

Specific features of the invention to which this application relates are set forth in the appended claims. The features and advantages of the present invention to which the present application relates will be better understood by reference to the exemplary embodiments and drawings described in detail below. A brief description of the drawings is as follows:

DETAILED DESCRIPTION OF THE INVENTION

Other advantages and effects of the present invention will become readily apparent to those skilled in the art from the following description of specific embodiments.

Definition of Terms

As used herein, the terms "construct" and "nucleic acid construct" are used interchangeably and generally refer to a nucleotide sequence including one or more functional units. The construct may be a DNA sequence, but multiple constructs can be provided on the same plasmid; examples of constructs may include but are not limited to, circular, linear, or double-stranded extrachromosomal DNA molecules, cosmids, and viral genomes containing non-native nucleotide sequences. The present invention provides a construct including a promoter, a multiple cloning site region, a CH1 fragment of a human IgG heavy chain constant region, a linker sequence, a yeast surface localization sequence, and optionally a tag sequence, e.g., a construct including nucleotide sequence shown in SEQ ID NO:1.

As used herein, the term "promoter" generally refers to a DNA sequence that regulates the expression of the DNA sequence to which the promoter is operably linked, thereby affecting the expression of the DNA sequence in a cell. The promoter will generally be suitable for the host cell in which the target gene is being expressed. For example, the promoter is a promoter that is expressed in both bacterial and yeast cells. The promoter may be from the yeast promoter database SCPD.

In the present application, the terms "multiple cloning site region", "multiple cloning site", "multiple cloning site regions" and "MCS" are used interchangeably and generally refer to a DNA sequence in a vector containing a plurality of restriction sites which serve as insertion sites for foreign DNA. MCS may be a short DNA sequence containing multiple restriction sites. Where each restriction enzyme site is usually unique, i.e. they often occur only once in a specific vector plasmid; the cleavage sites of different enzymes may overlap.

As used herein, the terms "linker" and "linker sequence" are used interchangeably and generally refer to a moiety that connects two or more discrete domains. A linker may allow discrete domains to exist independently. The linker moiety may be linear. Suitable linkers include polypeptides, polynucleic acids, and peptide nucleic acids. Exemplary linkers include polynucleotides encoding polypeptides, or polypeptides of amino acids or other non-naturally occurring moieties. The linker may be part of a native sequence, a variant, or a synthetic sequence thereof. For example, linker sequences in constructs provided herein may be glycine- and serine-rich linkers, such as $(Gly_4Ser)_3$ and $(GlySer)_5$.

As used herein, the term "yeast surface localization sequence" generally refers to a gene sequence of a protein in a vector that, when fused to a target protein sequence, is capable of localizing the target protein to the yeast cell surface using a yeast intracellular protein transport mechanism (e.g., GPI anchoring). Examples of yeast surface localization sequences include, but are not limited to, yeast cell wall mannoprotein gene, lectin gene, flocculatin Flo1p gene, AGα1, Aga1, Aga2, Flo1, Sed1p, Cwp1p, Cwp2p, Tip1p, Tir1p, and Srp1p.

As used herein, the term "tag" generally refers to a functional peptide that can be inserted into an expression vector such that one or more expression products of the construct are detected or readily purified. Such tags are well known in the art and may include radiolabelled amino acids or linkages to polypeptides of the biotinyl moiety. Examples include, but are not limited to, c-Myc, V5, hexahistidine, glutathione-S-transferase, streptavidin, biotin, hemagglutinin, Flag tag, and E tag. In the present application, the tag in the construct may further include a yeast selectable marker. The yeast selectable marker includes a drug-resistant marker and a genetic function that allows the yeast host cell to synthesize essential cellular nutrients (e.g., amino acids). Commonly used drug-resistant markers in yeast include chloramphenicol, kanamycin, methotrexate, and G418 (geneticin). The genetic function that allows yeast host cells to synthesize essential cellular nutrients is used with available yeast strains that have auxotrophic mutations in the corresponding genomic function. Typical yeast selectable markers include LEU2, TRP1, HIS3, HIS4, URA3, LIRAS, SFA1, ADE2, MET15, LYS5, LYS2, ILV2, FBA1, PSE1, PDI1, and PGK1. The methods for integrating vectors into yeast are well known, for example, see U.S. Pat. No. 7,479,389, W 02007136865, and PCT/US 2008/13719.

In the present application, the term "vector" is used to refer to a nucleic acid molecule capable of transporting a construct linked thereto, which may include plasmids, vectors, bacteriophages, cosmids or viruses, as well as bacterial artificial chromosomes (BACs) and yeast artificial chromosomes (YACs). Certain vectors are capable of autonomous replication in the host cell into which they are introduced, such as vectors having an origin of replication that functions in the host cell; other vectors can incorporate themselves into the genome of the host cell upon the introduction into the host cell, and thus replicate as the host genome replicates. The present invention provides a recombinant vector including the construct, for example, a recombinant vector including the nucleotide sequence shown in SEQ ID NO:1, which has the nucleotide sequence shown in SEQ ID NO:2.

In the present application, the "vector" is a yeast vector. Based on its replication pattern in yeast, the yeast vector includes five yeast vectors: Yip (yeast integration plasmid), YRp (yeast replication plasmid), YCp (yeast replication plasmid incorporating centromere element CEN), Yep (yeast-free plasmid), and YLp (yeast linear plasmid). Where, all of these plasmids, except the YLp plasmid, can be maintained in Escherichia coli as well as in Saccharomyces cerevisiae, and are therefore also referred to as yeast shuttle vectors. Examples of yeast vectors may include yeast 2 μm-rings and derivatives thereof, yeast vectors encoding yeast autonomous replication sequences, and yeast minichromosomes or yeast integration vectors.

In the present application, the terms "recombinant expression vector" and "expression vector" are used interchangeably and generally refer to a vector capable of directing the expression of a gene linked thereto; the expression vector may include any nucleic acid molecule for expressing a target protein in a cell. The expression vector may be any plasmid or vector known to those skilled in the art that is suitable for the expression of a protein in a specific host cell, including but not limited to mammalian cells, bacterial cells, and yeast cells. The present invention provides an expression vector obtained by inserting a target protein sequence into the recombinant vector.

As used herein, the term "recombinant" refers to materials that have been altered by human intervention (e.g., nucleic acids, genes, polynucleotides, polypeptides). For example, the elements in the recombinant molecule may not be native, or the arrangement of the elements in the recombinant molecule in the primary sequence may be altered to optimize expression and/or activity thereof. Reagents for producing recombinant molecules (e.g., recombinant nucleic acids) are common in the art. The term "recombinant" may also refer herein to a cell or organism including a recombinant molecule. For example, a host cell containing a recombinant nucleic acid. The present invention provides a recombinant vector containing the construct, an expression vector inserted with a target protein-coding sequence, and a host cell containing the expression vector. For example, a yeast cell containing the expression vector.

In some embodiments of the present invention, the yeast is selected from the group consisting of Saccharomyces cerevisiae, Saccharomyces Pastorianus, Saccharomyces bayanus, Kluyveromyces lactis, Kluyveromyces marxianus, Schizosaccharomyces pombe, Candida albicans, Pichia pastoris, Pichia stipitis, Yarrowia lipoidica, Hansenula polymorpha, Phaffia rhodozyma, Candida utilis, Arxula adeninivorans, Debaryomyces hansenii, Debaryomyces polymorphus, Schizosaccharomyces pombe, Schwanniomyces occidentalis or derivatives thereof.

In the present application, the term "library" generally refers to a collection or composition. The library may refer to a collection of encoded proteins or a collection of cells expressing the proteins. For example, an "antibody display library" may refer to a collection of large numbers of antibody proteins. A "host cell display library" may refer to a collection of large numbers of host cells expressing a recombinant target protein, such as a yeast display library.

As used herein, the term "display" refers generally to the act of expressing the protein, and sometimes also means that the expressed protein can be detected. For example, a recombinant host cell may display a modified polypeptide, which can be understood that the expression of the modified polypeptide is present in the cell and that the expressed modified polypeptide may be detected, for example, using cell immunoprecipitation or immunohybridization methods to detect the presence of the modified polypeptide in or on the surface of the cell.

In the present application, the term "include" generally refers to the inclusion of explicitly specified features, but not excluding other elements.

In the present application, the term "about" generally refers to a range from 0.5% to 10% above or below the specified value, for example, a range of 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, or 10% above or below the specified value.

In the present application, the term "rich" generally refers to a content of one or more substances of not less than 50%, for example, not less than 60%, 65%, 70%, 75%, 80%, 85%, 90%, 95%, 96%, 97%, 98%, 99%, 99.5%.

DETAILED DESCRIPTION OF THE INVENTION

Recombinant Vector

The present application provides a recombinant vector including the construct provided by the present invention. For example, the recombinant vector may be a vector including the construct of the sequence shown in SEQ ID NO:1. In a specific embodiment of the present application, a commercial yeast plasmid pYD1 is digested by using restriction endonucleases AgeI and PmeI, and then a vector which is relatively short in length but retains the replication function and the stable transcription ability of the plasmid in Escherichia coli and yeast cells is obtained through screening; the above-mentioned vector is combined with the above-mentioned synthetic construct, specifically a DNA fragment having the sequence shown in SEQ ID NO:1; and the recombinant vector pAN-HC having the sequence shown in SEQ ID NO:2 is obtained. The obtained recombinant vector may further infect competent cells to obtain a strain with the above-mentioned recombinant plasmid.

The recombinant vector provided by the present invention can be used as a tool vector and can be used for yeast display techniques. A coding sequence of a target protein is inserted into a multi-cloning site region of the recombinant vector to obtain a vector capable of expressing a modified polypeptide, and the modified polypeptide is fused with a protein sequence capable of positioning the target protein on the surface of a yeast cell, a tag sequence convenient for detection, a CH1 fragment of a human IgG heavy chain constant region and a linker sequence. For example, in a specific embodiment of the present invention, a human antibody gene fragment is amplified by designing primers and ligated or inserted into the multiple cloning site region of the vector pAN-HC to yield a recombinant vector.

Expression Vector

The present application provides an expression vector obtained by inserting a target protein sequence into the recombinant vector. When the target protein sequence includes an antigen-binding sequence, particularly a human antibody gene, the expression vector is an expression vector for expressing a fully human antibody. The human antibody gene sequence may include a human antibody gene heavy chain sequence, a human antibody gene light chain sequence, or a combination thereof.

In a specific embodiment of the present application, the primers can be designed according to a human antibody gene to amplify the human antibody gene fragment, and then the human antibody gene fragment is inserted into the recombinant vector pAN-HC to obtain an expression vector capable of expressing the human antibody. Validated by an antibody binding capacity experiment, the expression vector provided by the present application may be introduced into yeast cells, and the antibody protein capable of binding with the antigen may be expressed.

Host Cell

The recombinant vector containing the target protein-coding sequence is introduced into a host cell, and the recombinant host cell capable of expressing the modified polypeptide may be obtained through screening. If the expressed modified polypeptide is capable of being localized on the surface of the host cell, the recombinant host cell may serve as a surface-displaying host cell.

In a specific embodiment of the present application, a human TIGIT protein antibody sequence is inserted into the vector pAN-HC, yeast cells introduced with the above-mentioned TIGIT antibody expression vector can generate TIGIT antibody which can bind to the added human TIGIT recombinant protein. The results show that the recombinant yeast cells containing the vector pAN-HC could function as the expression vector of antibody, and the produced antibodies have antigen affinity.

Host Cell Display Library

One or more modified polypeptides may be present in a host cell. For example, the recombinant host cell may display at least $10^2$, at least $10^3$, at least $10^4$, or at least $10^5$ the modified polypeptide sequences. A plurality of the above-mentioned recombinant host cells may constitute a host cell display library. Several modified polypeptides may be displayed in the host cell display library. For example, the host cell display library may display at least $10^2$, at least $10^4$, at least $10^6$, or at least $10^8$ the modified polypeptides.

In a specific embodiment of the present application, human antibody gene heavy chain family including H1, H2, H3, H4, and H5, kappa light chain family including κ1, κ2, and κ3, and lambda light chain family including λ1, λ2, and λ3 fragments are inserted into vector pAN-HC; and a heavy chain fragment expression vector and a light chain fragment expression vector are introduced into the same recombinant yeast cell simultaneously. By combining and pairing different heavy chain fragments and light chain fragments, an antibody library with antibody gene diversity may be obtained. Since the modified polypeptide expressed by the vector pAN-HC used in this embodiment can be localized to the outer surface of the cell membrane, a yeast display antibody library is formed.

Construction Method and Kit

The present application provides a cell construction method, which includes the following steps: a) inserting a coding sequence of a target protein into a vector V0 to obtain a recombinant vector V1; and b) introducing the recombinant vector V1 into cells. Where the vector V0 may have the nucleotide sequence shown in SEQ ID NO: 2; the cells are bacterial cells and/or yeast cells; the resulting cell produces a modified polypeptide that is a fusion protein of the target protein. The methods of introducing recombinant vectors into cells and screening positive cells into which the recombinant vectors are introduced are well known to those skilled in the art.

The present application also provides a kit that can be used for constructing the recombinant expression vector. The kit may include the recombinant vector; further include nucleic acids containing a target protein-coding sequence or primers from which the target protein-coding sequence may be amplified. The kit may also contain other reagents for inserting the target nucleic acid into the vector, such as restriction endonucleases, and DNA ligases.

Without intending to be bound by any theory, the following examples are intended merely to illustrate the fusion proteins, methods of preparation, uses, etc., of the present application and are not intended to limit the scope of the present application.

The present application comprises the following embodiments:

1. A construct comprising a promoter, a multiple cloning site region, a CH1 fragment of a human IgG heavy chain constant region, a linker sequence, a yeast surface localization sequence, and optionally a tag sequence.

2. The construct according to embodiment 1, comprising the structure of Expression (I):

Expression (I):

5'-A-B-C-D-E-F-3'  (I);

wherein,

A represents the promoter;
B represents the multiple cloning site region;
C represents the CH1 fragment of the human IgG heavy chain constant region;
D represents the linker sequence;
E represents the yeast surface positioning sequence; and
F represents none or the tag sequence.

3. The construct according to embodiment 1 or 2, wherein the promoter is selected from the group consisting of yeast GAL1 promoter, yeast GAL10 promoter, and yeast GAL1/GAL10 bidirectional promoter.

4. The construct according to any one of the embodiments 1-3, wherein the linker sequence is a glycine- and serine-rich linker.

5. The construct according to any one of the embodiments 1-4, wherein the linker is selected from the group consisting of $(Gly_4Ser)_3$ and $(GlySer)_5$.

6. The construct according to any one of the embodiments 1-5, wherein the yeast surface localization sequence is selected from the group consisting of Aga1p polypeptide or fragment thereof, Aga2p polypeptide or fragment thereof, and Sag1p polypeptide or fragment thereof.

7. The construct according to any one of the embodiments 1-6, wherein the tag sequence is selected from the group consisting of c-Myc, V5, hexahistidine, glutathione-S-transferase, streptavidin, biotin, hemagglutinin, Flag tag and E tag.

8. The construct according to any one of the embodiments 1-7, comprising the nucleotide sequence shown in SEQ ID NO:1.

9. Use of the construct according to any one of the embodiments 1-8 in the preparation of a recombinant vector.

10. The use according to embodiment 9, wherein the recombinant vector may be replicated and expressed in bacterial and yeast host cells.

11. A recombinant vector comprising the construct according to any one of the embodiments 1-8.

12. The recombinant vector according to embodiment 11, comprising the nucleotide sequence shown in SEQ ID NO:1.

13. The recombinant vector according to embodiment 11 or embodiment 12, wherein the vector is selected from the group consisting of plasmids, vectors, phages, cosmids, and viruses.

14. The recombinant vector according to embodiment 13, wherein the plasmid is a yeast plasmid.

15. The recombinant vector according to embodiment 14, wherein the yeast plasmid is selected from the group consisting of yeast integration plasmids, yeast replication plasmids, yeast replication plasmids incorporating centromere elements, yeast-free plasmids, and yeast linear plasmids.

16. The recombinant vector according to any one of the embodiments 11-15, comprising the nucleotide sequence shown in SEQ ID NO:2.

17. A kit comprising the recombinant vector according to any one of the embodiments 11-16.

18. The kit according to embodiment 17, further comprising one or more reagents selected from the group consisting of primers, endonucleases, and DNA ligases.

19. The kit according to embodiment 18, wherein the primers are used to amplify a target protein sequence.

20. The kit according to embodiment 18 or 19, wherein the primer comprises the primers with the sequences shown in SEQ ID NO:3-SEQ ID NO:20.

21. The kit according to any one of the embodiments 17-20, wherein the recombinant vector comprises the nucleotide sequence shown in SEQ ID NO:2.

22. The kit according to any one of the embodiments 19-21 for inserting the target protein sequence into the recombinant vector.

23. Use of the kit according to any one of the embodiments 17-22 in the preparation of an expression vector for a target protein.

24. An expression vector obtained by inserting a target protein sequence into the recombinant vector according to any one of the embodiments 11-16.

25. The expression vector according to embodiment 24, wherein the target protein sequence comprises an antigen-binding sequence.

26. The expression vector according to embodiment 25, wherein the antigen-binding sequence is selected from the group consisting of heavy chains, light chains, heavy chain-light chain dimers, Fab fragments, F(ab')2 fragments, Fv fragments, single chain Fv(scFv), and dAb.

27. The expression vector according to embodiment 25 or 26, wherein the antigen-binding sequence is a human antibody gene sequence.

28. The expression vector according to embodiment 27, wherein the human antibody gene sequence comprises human antibody gene heavy chain sequences, human antibody gene light chain sequences, or combination thereof.

29. The expression vector according to embodiment 28, wherein the human antibody gene light chain sequence is selected from the group consisting of human kappa light chain gene sequence and human lambda light chain gene sequence.

30. The expression vector according to any one of the embodiments 24-29, wherein the vector is prepared using the kit according to embodiment 17.

31. Use of the expression vector according to any one of the embodiments 24-30 in the preparation of yeast display cells.

32. A cell construction method comprising:
a) inserting a target protein sequence into the vector V0 according to any one of the embodiments 24-30 to obtain an expression vector V1; and
b) introducing the expression vector V1 obtained in step a) into a host cell to obtain a recombinant host cell.

33. The method according to embodiment 32, wherein the vector V0 comprises the nucleotide sequence shown in SEQ ID NO:2.

34. The method according to embodiment 32 or 33, wherein the host cell is a yeast cell.

35. The method according to embodiment 34, wherein the yeast cell is selected from the group consisting of *Saccharomyces cerevisiae*, *Pichia pastoris*, and derivatives thereof.

36. The method according to any one of the embodiments 32-35, wherein the target protein is expressed on the surface of the recombinant host cell obtained in step b).

37. A host cell comprising the expression vector according to any one of the embodiments 24-30.

38. The host cell according to embodiment 37, wherein the host cell is constructed according to the method according to any one of embodiments 32-36.

39. The host cell according to embodiment 36 or embodiment 37, wherein the host cell expresses at least $10^2$, at least $10^3$, at least $10^4$, or at least $10^5$ target proteins.

40. The host cell according to embodiment 39, wherein the target protein is an antibody or an antigen-binding protein.

41. The host cell according to embodiment 40, wherein the antibody or antigen-binding protein is a human antibody or an antigen-binding protein.

42. The host cell according to any one of the embodiments 37-41, wherein the host cell is a yeast cell expressing a fully human antibody or an antigen-binding protein.

43. The host cell according to embodiment 42, wherein the yeast cell is a yeast display cell expressing a fully human antibody or an antigen-binding protein.

44. A host cell display library comprising at least two host cells according to any one of the embodiments 37-43.

45. The host cell display library according to embodiment 44, wherein the library is a yeast cell display library.

46. The host cell display library according to embodiment 44 or 45, wherein the library provides an antibody display library.

47. The host cell display library according to any one of the embodiments 44-46, wherein the library displays at least $10^2$, at least $10^4$, at least $10^6$, or at least $10^8$ fully human antibodies or antigen-binding proteins.

EXAMPLES

Example 1 Construction of Recombinant Expression Vector pAN-HC

A recombinant expression vector with a human IgG heavy chain constant region was constructed using the commercial plasmid pYD1 (available from Invitrogen). The brief operation was as follows:

(1) The commercial plasmid pYD1 was digested with endonucleases AgeI and PmeI for 1 h at 37° C.; the larger fragments were then recovered using an agarose gel.

Figure 1:
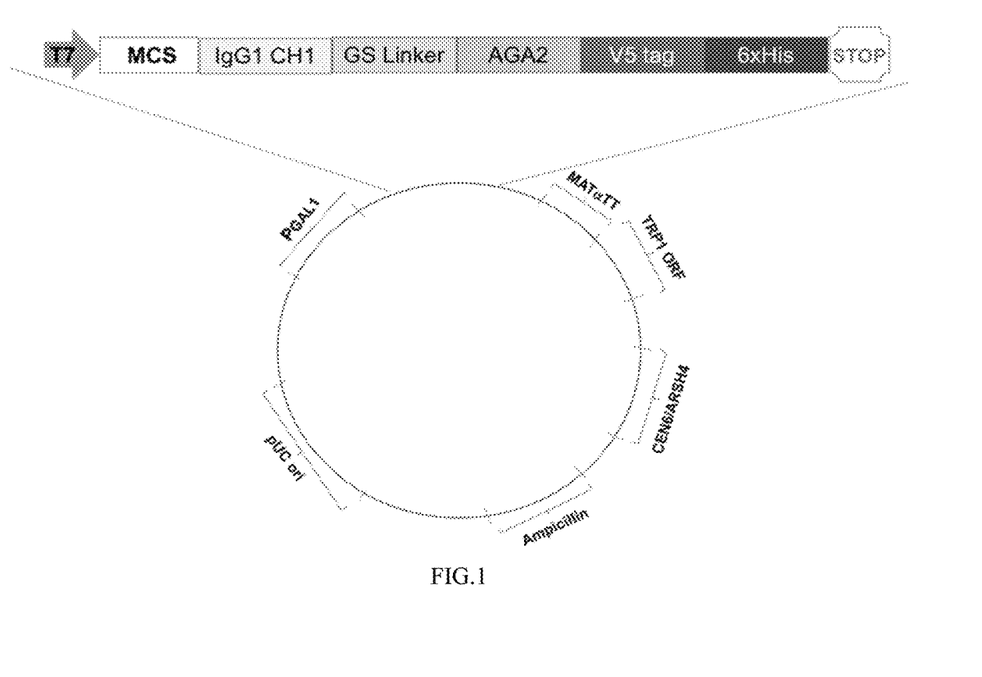
FIG. 1 shows a schematic diagram of the construct described herein.

(2) A segment of the nucleotide sequence (available from ThermoFisher) shown in SEQ ID NO:2 was artificially synthesized. The elements contained in this sequence were shown in FIG. 1.

(3) The purified vector fragments recovered in step (1) and the fragment synthesized in step (2) were ligated using an In-fusion Cloning kit (available from Takara Bio Inc.).

(4) The ligation product in step (3) was transformed into bacteria, and positive clones were screened and sequenced for identification.

The recombinant expression vector pAN-HC without any mutation in the sequence was obtained by sequencing and screening, with the sequence shown in SEQ ID NO:2.

Example 2 Expression of the Antibody with an Expression Vector Constructed Using the Recombinant Vector pAN-HC The pAN-HC recombinant vector obtained in Example 1 was tested using known TIGIT antibody sequences to evaluate the antibody expression ability of this recombinant vector.

(1) A nucleotide sequence of a segment of human TIGIT antibody (available from ThermoFisher) was provided.

(2) The recombinant vector pAN-HC was digested with DNA restriction endonucleases NheI and Eco47III and large fragments were recovered.

(3) The antibody and vector sequences in steps (1) and (2) were transferred to yeast strain EBY100 by electrotransformation of yeast.

(4) The yeast strain was cultured overnight with 100 ml tryptophan-deficient medium SD-CAA (tyrosine 5 g/L, glucose 20 g/L, amino acid-free and ammonium sulfate-free yeast nitrogen base 1.7 g/L, ammonium sulfate 5.3 g/L, $Na_2HPO_4$-$7H_2O$ 10.2 g/L, $NaH_2PO_4$—$H_2O$ 8.6 g/L), and the yeast containing the recombinant plasmid was screened.

(5) 2 mL of the yeast culture solution was taken from step (4), followed by centrifuging at 3000 rpm for 5 min and removing the supernatant, and the antibody was induced overnight using 5 mL of induction medium SGR-CAA (tyrosine 5 g/L, glucose 1 g/L, raffinose 20 g/L, galactose 20 g/L, amino acid-free and ammonium sulfate-free yeast nitrogen base 1.7 g/L, ammonium sulfate 5.3 g/L, $Na_2HPO_4$-$7H_2O$ 10.2 g/L, $NaH_2PO_4$—$H_2O$ 8.6 g/L).

(6) 500 μL of yeast culture solution was taken from step (5), followed by centrifuging at 3000 rpm for 5 min, removing the supernatant, and retaining yeast precipitate; the yeast precipitate was then resuspended in a solution containing FITC-labeled V5 antibody, and placed in a 4° C. freezer for 30 mins.

(7) The yeast precipitate was washed once with PBS, the final yeast precipitate was resuspended in 1 mL of PBS, and antibody expression was detected by a flow cytometer.

Figure 2:
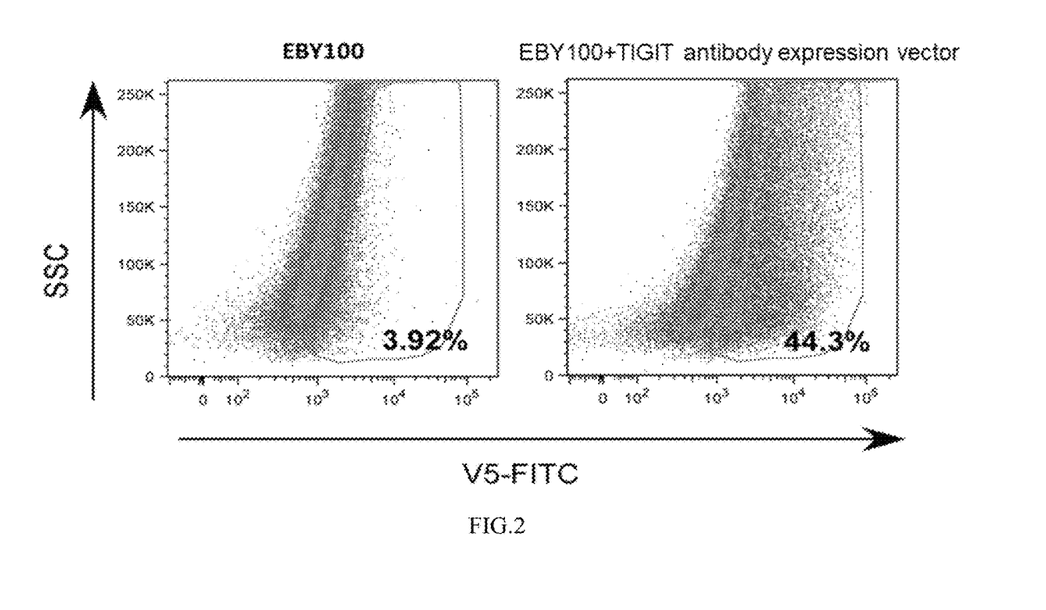
FIG. 2 shows the results of flow cytometry analysis of FITC-labeled yeast cells in a verification assay of antibodies expressed by the recombinant vector pAN-HC described herein.

Results: As shown in FIG. 2, there was no FITC signal in EBY100 yeast without expression vector, while there was FITC signal in yeast electrotransformed with TIGIT antibody expression vector, which showed that the recombinant expression vector pAN-HC could express the antibody, and the expressed antibody could be well displayed on the surface of yeast.

Example 3 Verification of the Binding Ability of Antibody Expressed by the Expression Vector Constructed Using Recombinant Vector pAN-HC PAN-HC was used to express the antibody to verify whether it can bind to the target protein TIGIT.

(1) 500 μL of induced overnight yeast culture solution was taken from step (5) in Example 2, followed by centrifuging at 3000 rpm for 5 min, removing the supernatant, and retaining yeast precipitate. The yeast precipitate was resuspended in 500 μL of PBS, 100 nM biotinylated human TIGIT recombinant protein was added, and the mixture was incubated for 1 hour at room temperature.

(2) The incubated mixture was centrifuged under the same conditions and then resuspended in 1 mL of PBS; the above washing step was repeated 3 times.

(3) Since the antibody in Example 2 had a V5 tag, the yeast precipitate was resuspended with a solution containing FITC-labeled V5 antibody and PE-labeled streptavidin, and placed in a 4° C. freezer for 30 min.

(4) Step (2) was repeated.

(5) The yeast precipitate was resuspended in 500 μL of PBS.

Figure 3:
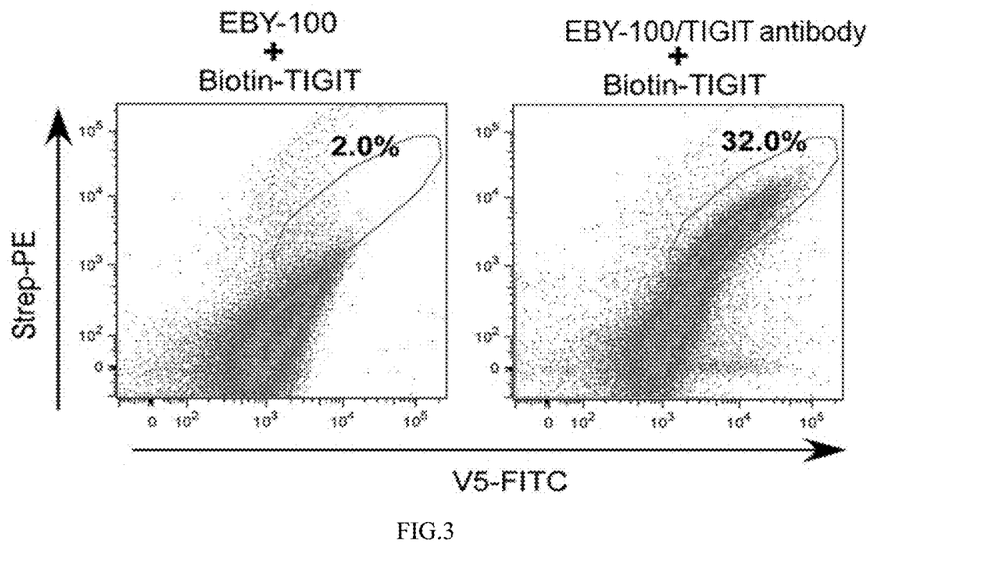
FIG. 3 shows the results of flow cytometry analysis of FITC- and PE-labeled yeast cells in a binding capacity assay of antibodies expressed by the recombinant vector pAN-HC described herein.

Results: Since the antibody displayed on the yeast surface may be labeled with FITC and the TIGIT recombinant protein may be labeled with PE, if both FITC and PE could be present on the yeast surface, the antibody displayed by yeast could bind to the TIGIT recombinant protein; the resulting group was shown in the left plane, and the yeast culture solution in Example 2 was shown in the right plane of FIG. 3; the control group showed that there was no FITC signal, i.e. no antibody expression in yeast; and there was no PE signal, i.e. no TIGIT attached to the cell membrane; while in the experimental group, the presence of both FITC and PE signals on the yeast surface demonstrated that TIGIT protein was detected on the yeast surface by binding to antibodies on the yeast surface.

Example 4 Construction and Analysis of Yeast Display Antibody Library

A yeast display antibody library was constructed using the recombinant expression vector pAN-HC.

4.1 Primers for PCR cloning of human antibody genes linked to the recombinant expression vector pAN-HC were designed according to heavy chain family including H1, H2, H3, H4 and H5, kappa light chain family including κ1, κ2 and κ3, and lambda light chain family including λ1, λ2 and λ3, respectively.

| Sequence Number | Amplified fragments | Primer sequence |
| --- | --- | --- |
| 1 | Human antibody heavy chain H1 | SEQ ID NO: 3 and SEQ ID NO: 4 |
| 2 | Human antibody heavy chain H2 | SEQ ID NO: 5 and SEQ ID NO: 4 |
| 3 | Human antibody heavy chain H3 | SEQ ID NO: 6 and SEQ ID NO: 7 |
| 4 | Human antibody heavy chain H4 | SEQ ID NO: 8 and SEQ ID NO: 9 |
| 5 | Human antibody heavy chain H5 | SEQ ID NO: 10 and SEQ ID NO: 9 |
| 6 | Human antibody kappa light chain κ1 | SEQ ID NO: 13 and SEQ ID NO: 14 |
| 7 | Human antibody kappa light chain κ2 | SEQ ID NO: 13 and SEQ ID NO: 14 |
| 8 | Human antibody kappa light chain κ3 | SEQ ID NO: 15 and SEQ ID NO: 16 |
| 9 | Human antibody lambda light λ1 | SEQ ID NO: 17 and SEQ ID NO: 18 |
| 10 | Human antibody lambda light λ2 | SEQ ID NO: 19 and SEQ ID NO: 18 |
| 11 | Human antibody lambda light λ3 | SEQ ID NO: 20 and SEQ ID NO: 18 |

4.2 Immune cell-rich mRNA (available from Takara) was used as a source of antibody gene. mRNA was reverse transcribed into cDNA using the SMARTer PCR cDNA Synthesis Kit (available from Clontech) according to its instructions. The antibody gene nucleic acid fragment was obtained by using the obtained cDNA as a template, and performing PCR amplification by using the primers.

The PCR reaction system was as follows: 100 μL of a total volume including 2 μL of cDNA template, each 2 μL of 20 μM primers (forward and reverse primers), 1 μL of AccuPrime Pfx DNA Polymerase (100 μL, 2.5 U/μL), 10 μL of 10× AccuPrime reaction mix, and 83 μL of purified deionized water. The PCR reaction conditions were as follows: 94° C., 30 seconds/56° C., 30 seconds/68° C., 45 seconds, 30 cycles.

Figure 4:
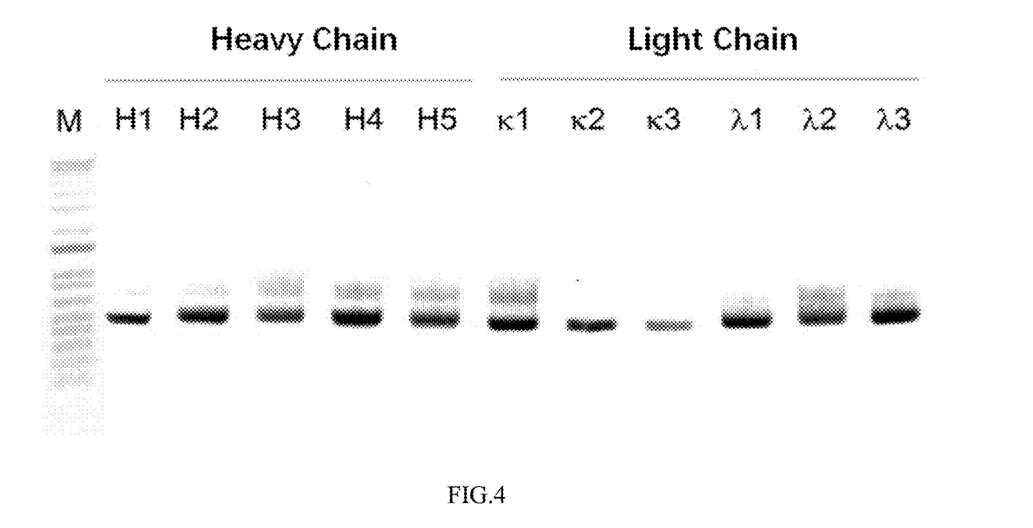
FIG. 4 shows the electrophoresis results of the human antibody fragment obtained by specific amplification with the primer pair described herein.

Results: as shown in FIG. 4, all of the heavy chain genes (H1 to H5) and light chain genes (κ1, κ2, κ3 and λ1, λ2, λ3) tested were specifically amplified, while the size of the PCR products was consistent with that expected, indicating that the primers were designed for the intended purpose.

Figure 5:
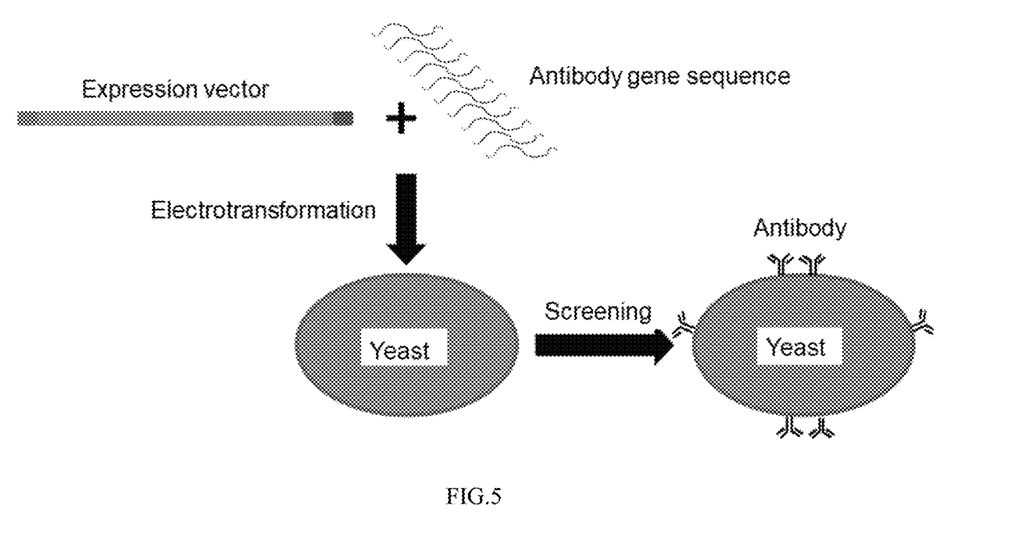
FIG. 5 shows a schematic diagram of the yeast display library described herein.

4.3 A schematic diagram for constructing the yeast display library was shown in FIG. 5, and the specific steps were as follows:

(1) The recombinant vector pAN-HC was digested with the DNA restriction endonucleases NheI and EcoR 47 III, and the vector was recovered.

(2) The heavy chain gene and the light chain gene were amplified respectively by using the PCR reaction and the gene amplification conditions in step 2, and PCR amplification products were purified.

(3) Electrotransformation of yeast: the entire yeast display library contained 10 antibody repertoires in which each heavy chain will be paired separately with two different types of light chains. If heavy chain H1 was paired with light chains κ1, κ2, and κ3, while heavy chain H1 was also paired with light chains λ1, λ2, and λ3, and so on (a total of five heavy chains may form 10 antibody repertoires). Each antibody repertoire consisted of 50 electrotransformations, with 10 μg of vector, 10 μg of heavy chain gene, and 10 μg of light chain gene mixture (at a ratio of 1:1:1) per electrotransformation.

(4) To test whether the yeast display library successfully introduced the antibody gene into the expression vector and to have a preliminary understanding of the antibody gene diversity in the antibody library, some yeast strains were randomly selected, DNA in yeast was extracted using Yeast DNA Extract Kit (available from Thermofisher), and the antibody gene was sequenced.

Figure 6:
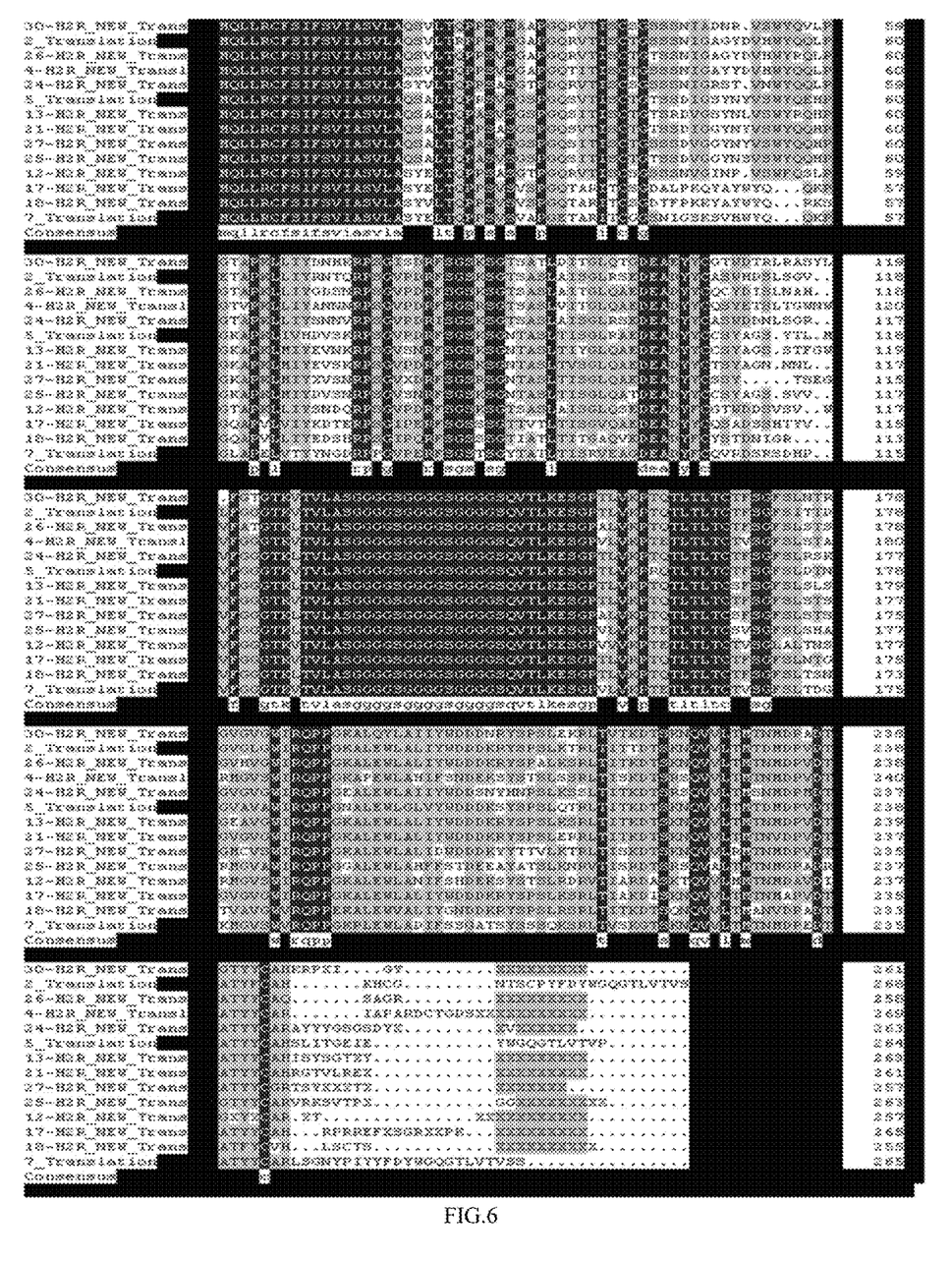
FIG. 6 shows the sequencing results of randomly selected yeast clones in the yeast display library described herein.

Results: The sequencing results were shown in FIG. 6, and 14 randomly selected yeast clones all contained antibody genes with correct sequences without any repeatability, demonstrating that the yeast display library was successfully constructed, and also the antibody library of the scheme had good diversity.

What is claimed is:

1. A polynucleotide construct comprising the nucleotide sequence of SEQ ID NO:1, the polynucleotide construct comprising the structure of Expression (I), wherein Expression (I) comprises:

5'-A-B-C-D-E-F-3'  (I); wherein,

A represents the promoter;
B represents the multiple cloning site region;
C represents the $CH_1$ fragment of the human IgG heavy chain constant region;
D represents the linker sequence, wherein the linker is selected from the group consisting of $(Gly_4Ser)_3$ and $(GlySer)_5$;
E represents the yeast surface positioning sequence; and
F represents none or the tag sequence, wherein the tag sequence is selected from the group consisting of c-Myc, V5, hexahistidine, glutathione-S-transferase, streptavidin, biotin, hemagglutinin, Flag tag and E tag.

2. A recombinant vector comprising the construct according to claim 1.

3. The recombinant vector according to claim 2, wherein the vector is selected from the group consisting of plasmids, vectors, phages, cosmids, and viruses;
wherein the plasmid is a yeast plasmid; wherein the yeast plasmid is selected from the group consisting of yeast integration plasmids, yeast replication plasmids, yeast replication plasmids incorporating centromere elements, yeast-free plasmids, and yeast linear plasmids.

4. The recombinant vector according to claim 2, comprising the nucleotide sequence shown in SEQ ID NO:2.

5. A kit comprising the recombinant vector according to claim 2.

6. The kit according to claim 5, wherein the kit further comprises one or more reagents selected from the group consisting of primers, endonucleases, and DNA ligases, wherein the primer comprises the primers with the sequences shown in SEQ ID NO:3-SEQ ID NO:20.

7. The kit according to claim 5, wherein the recombinant vector comprises the nucleotide sequence shown in SEQ ID NO:2.

8. An expression vector obtained by inserting a target protein sequence into the recombinant vector according to claim 2;
wherein the target protein sequence comprises an antigen-binding sequence, wherein the antigen-binding sequence is selected from the group consisting of heavy chains, light chains, heavy chain-light chain dimers, Fab fragments, F(ab')2 fragments, Fv fragments, single chain Fv(scFv), and dAb.

9. The expression vector according to claim 8, wherein the antigen-binding sequence is a human antibody gene sequence, wherein the human antibody gene sequence comprises human antibody gene heavy chain sequences, human antibody gene light chain sequences, or combination thereof.

10. A cell construction method comprising:
a) inserting a target protein sequence into the vector V0 according to claim 7 to obtain an expression vector V1; and
b) introducing the expression vector V1 obtained in step a) into a host cell to obtain a recombinant host cell.

11. The method according to claim 10, wherein the vector V0 comprises the nucleotide sequence shown in SEQ ID NO:2.

12. The method according to claim 10, wherein the host cell is a yeast cell, wherein the yeast cell is selected from the group consisting of *Saccharomyces cerevisiae, Pichia pastoris*, and derivatives thereof.

13. The method according to claim 10, wherein the target protein is expressed on the surface of the recombinant host cell obtained in step b).

14. A host cell comprising the expression vector according to claim 8.

15. A host cell display library comprising at least two host cells according to claim 8.

16. The host cell display library according to claim 14, wherein the library provides an antibody display library, wherein the library displays at least $10^2$, at least $10^4$, at least $10^6$, or at least at least $10^8$ fully human antibodies or antigen-binding proteins.

* * * * *

SEQUENCE LISTING

```
<160> NUMBER OF SEQ ID NOS: 20

<210> SEQ ID NO 1
<211> LENGTH: 1210
<212> TYPE: DNA
<213> ORGANISM: Artificial Sequence
<220> FEATURE:
<223> OTHER INFORMATION: Construct

<400> SEQUENCE: 1
gcgtcctcgt cttcaccggt cgcgttcctg aaacgcagat gtgcctcgcg ccgcactgct      60
ccgaacaata aagattctac aatactagct tttatggtta tgaagaggaa aaattggcag     120
taacctggcc ccacaaacct tcaaatgaac gaatcaaatt aacaaccata ggatgataat     180
gcgattagtt ttttagcctt atttctgggg taattaatca gcgaagcgat gatttttgat     240
ctattaacag atatataaat gcaaaaactg cataaccact ttaactaata ctttcaacat     300
tttcggtttg tattacttct tattcaaatg taataaaagt atcaacaaaa aattgttaat     360
atacctctat actttaacgt caaggagaaa aaacccggga tcggactact agcagctgta     420
atacgactca ctagggaa tattaagcta attctacttc atacattttc aattaagatg     480
cagttacttc gctgttttc aatatttct gttattgcta gcgttttagc aagcgctagt     540
accaagggcc catcggtctt cccctggca ccctcctcca agagcacctc tggggcaca     600 gcggccctgg gctgcctggt caaggactac ttccccgaac cggtgacggt gtcgtggaac     660
tcaggcgccc tgaccagcgg cgtgcacacc ttcccggctg tcctacagtc ctcaggactc     720
tactccctca gcagcgtggt gaccgtgccc tccagcagct gggcaccca gacctacatc     780 tgcaacgtga atcacaagcc cagcaacacc aaggtggaca agaaagttga gcccaaatct     840
tgtgctagtg gtggtggtgg ctctggtggt ggcggttctg gtggcggtgg ttctcaggaa     900
ctgacaacta tatgcgagca aatcccctca ccaactttag aatcgacgcc gtactctttg     960
tcaacgacta ctattttggc caacgggaag gcaatgcaag gagttttttga atattacaaa    1020 tcagtaacgt ttgtcagtaa ttgcggttct caccccctcaa caactagcaa aggcagcccc    1080
ataaacacac agtatgttt ttctagaggg cccttcgaag gtaagcctat ccctaaccct    1140
ctcctcggtc tcgattctac gcgtaccggt catcatcacc atcaccattg agtttaaacc    1200
cgctgatctg                                                           1210

<210> SEQ ID NO 2
<211> LENGTH: 5192
<212> TYPE: DNA
```

<213> ORGANISM: Artificial Sequence
<220> FEATURE:
<223> OTHER INFORMATION: Vector

<400> SEQUENCE: 2

| | | | | | |
|---|---|---|---|---|---|
| acggattaga | agccgccgag | cgggtgacag | ccctccgaag | gaagactctc | ctccgtgcgt | 60 |
| cctcgtcttc | accggtcgcg | ttcctgaaac | gcagatgtgc | ctcgcgccgc | actgctccga | 120 |
| acaataaaga | ttctacaata | ctagctttta | tggttatgaa | gaggaaaaat | tggcagtaac | 180 |
| ctggccccac | aaaccttcaa | atgaacgaat | caaattaaca | accataggat | gataatgcga | 240 |
| ttagtttttt | agccttattt | ctggggtaat | taatcagcga | agcgatgatt | tttgatctat | 300 |
| taacagatat | ataaatgcaa | aaactgcata | accactttaa | ctaatacttt | caacattttc | 360 |
| ggtttgtatt | acttcttatt | caaatgtaat | aaaagtatca | acaaaaaatt | gttaatatac | 420 |
| ctctatactt | taacgtcaag | gagaaaaaac | cccggatcgg | actactagca | gctgtaatac | 480 |
| gactcactat | agggaatatt | aagctaattc | tacttcatac | attttcaatt | aagatgcagt | 540 |
| tacttcgctg | ttttcaata | ttttctgtta | ttgctagcgt | tttagcaagc | gctagtacca | 600 |
| agggcccatc | ggtcttcccc | ctggcaccct | cctccaagag | cacctctggg | ggcacagcgg | 660 |
| ccctgggctg | cctggtcaag | gactacttcc | ccgaaccggt | gacggtgtcg | tggaactcag | 720 |
| gcgccctgac | cagcggcgtg | cacaccttcc | cggctgtcct | acagtcctca | ggactctact | 780 |
| ccctcagcag | cgtggtgacc | gtgccctcca | gcagcttggg | cacccagacc | tacatctgca | 840 |
| acgtgaatca | caagcccagc | aacaccaagg | tggacaagaa | agttgagccc | aaatcttgtg | 900 |
| ctagtggtgg | tggtggctct | ggtggtggcg | gttctggtgg | cggtggttct | caggaactga | 960 |
| caactatatg | cgagcaaatc | ccctcaccaa | ctttagaatc | gacgccgtac | tctttgtcaa | 1020 |
| cgactactat | tttggccaac | gggaaggcaa | tgcaaggagt | ttttgaatat | acaaatcag | 1080 |
| taacgtttgt | cagtaattgc | ggttctcacc | cctcaacaac | tagcaaaggc | agccccataa | 1140 |
| acacacagta | tgttttttct | agagggcct | tcgaaggtaa | gcctatccct | aaccctctcc | 1200 |
| tcggtctcga | ttctacgcgt | accggtcatc | atcaccatca | ccattgagtt | taaacccgct | 1260 |
| gatctgataa | caacagtgta | gatgtaacaa | aatcgacttt | gttcccactg | tacttttagc | 1320 |
| tcgtacaaaa | tacaatatac | ttttcatttc | tccgtaaaca | acatgttttc | ccatgtaata | 1380 |
| tccttttcta | tttttcgttc | cgttaccaac | tttacacata | ctttatatag | ctattcactt | 1440 |
| ctatacacta | aaaaactaag | acaattttaa | ttttgctgcc | tgccatattt | caatttgtta | 1500 |
| taaattccta | taatttatcc | tattagtagc | taaaaaaaga | tgaatgtgaa | tcgaatccta | 1560 |
| agagaattgg | gcaagtgcac | aaacaatact | taaataaata | ctactcagta | ataacctatt | 1620 |
| tcttagcatt | tttgacgaaa | tttgctattt | tgttagagtc | ttttacacca | tttgtctcca | 1680 |
| cacctccgct | tacatcaaca | ccaataacgc | catttaatct | aagcgcatca | ccaacatttt | 1740 |
| ctggcgtcag | tccaccagct | aacataaaat | gtaagctctc | ggggctctct | tgccttccaa | 1800 |
| cccagtcaga | aatcgagttc | caatccaaaa | gttcacctgt | cccacctgct | tctgaatcaa | 1860 |
| acaagggaat | aaacgaatga | ggtttctgtg | aagctgcact | gagtagtatg | ttgcagtctt | 1920 |
| ttggaaatac | gagtctttta | ataactggca | aaccgaggaa | ctcttggtat | tcttgccacg | 1980 |
| actcatctcc | gtgcagttgg | acgatatcaa | tgccgtaatc | attgaccaga | gccaaaacat | 2040 |
| cctccttagg | ttgattacga | aacacgccaa | ccaagtattt | cggagtgcct | gaactatttt | 2100 |
| tatatgcttt | tacaagactt | gaaatttccc | ttgcaataac | cgggtcaatt | gttctctttc | 2160 |
| tattgggcac | acatataata | cccagcaagt | cagcatcgga | atctagagca | cattctgcgg | 2220 |

```
cctctgtgct ctgcaagccg caaactttca ccaatggacc agaactacct gtgaaattaa    2280
taacagacat actccaagct gcctttgtgt gcttaatcac gtatactcac gtgctcaata    2340
gtcaccaatg ccctccctct tggccctctc cttttctttt ttcgaccgaa tttcttgaag    2400
acgaaagggc ctcgtgatac gcctattttt ataggttaat gtcatgataa taatggtttc    2460
ttaggacgga tcgcttgcct gtaacttaca cgcgcctcgt atcttttaat gatggaataa    2520
tttgggaatt tactctgtgt ttatttattt ttatgttttg tatttggatt ttagaaagta    2580
aataaagaag gtagaagagt tacggaatga agaaaaaaaa ataaacaaag gtttaaaaaa    2640
tttcaacaaa aagcgtactt tacatatata tttattagac aagaaaagca gattaaatag    2700
atatacattc gattaacgat aagtaaaatg taaaatcaca ggattttcgt gtgtggtctt    2760
ctacacagac aagatgaaac aattcggcat taatacctga gagcaggaag agcaagataa    2820
aaggtagtat tgttggcga tccccctaga gtcttttaca tcttcggaaa acaaaaacta    2880
tttttctttt aatttctttt tttacttcct attttaatt tatatattta tattaaaaaa    2940
tttaaattat aattattttt atagcacgtg atgaaaagga cccaggtggc acttttcggg    3000
gaaatgtgcg cggaacccct atttgtttat ttttctaaat acattcaaat atgtatccgc    3060
tcatgagaca ataaccctga taaatgcttc aataatattg aaaaggaag agtatgagta    3120 ttcaacattt ccgtgtcgcc cttattccct ttttgcggc attttgcctt cctgtttttg    3180
ctcacccaga aacgctggtg aaagtaaaag atgctgaaga tcagttgggt gcacgagtgg    3240
gttacatcga actggatctc aacagcggta agatccttga gagttttcgc cccgaagaac    3300
gttttccaat gatgagcact tttaaagttc tgctatgtgg cgcggtatta tcccgtgttg    3360
acgccgggca agagcaactc ggtcgccgca tacactattc tcagaatgac ttggttgagt    3420
actcaccagt cacagaaaag catcttacgg atggcatgac agtaagagaa ttatgcagtg    3480
ctgccataac catgagtgat aacactgcgg ccaacttact tctgacaacg atcggaggac    3540
cgaaggagct aaccgctttt ttgcacaaca tgggggatca tgtaactcgc cttgatcgtt    3600
gggaaccgga gctgaatgaa gccataccaa acgacgagcg tgacaccacg atgcctgtag    3660
caatggcaac aacgttgcgc aaactattaa ctggcgaact acttactcta gcttcccggc    3720
aacaattaat agactggatg gaggcggata aagttgcagg accacttctg cgctcggccc    3780
ttccggctgg ctggtttatt gctgataaat ctggagccgg tgagcgtggg tctcgcggta    3840
tcattgcagc actggggcca gatggtaagc cctcccgtat cgtagttatc tacacgacgg    3900
gcagtcaggc aactatggat gaacgaaata gacagatcgc tgagataggt gcctcactga    3960
ttaagcattg gtaactgtca gaccaagttt actcatatat actttagatt gatttaaaac    4020
ttcattttta atttaaaagg atctaggtga agatccttt tgataatctc atgaccaaaa    4080
tcccttaacg tgagttttcg ttccactgag cgtcagaccc cgtagaaaag atcaaaggat    4140
cttcttgaga tccttttttt ctgcgcgtaa tctgctgctt gcaaacaaaa aaaccaccgc    4200
taccagcggt ggtttgtttg ccggatcaag agctaccaac tcttttccg aaggtaactg    4260 gcttcagcag agcgcagata ccaaatactg tccttctagt gtagccgtag ttaggccacc    4320
acttcaagaa ctctgtagca ccgcctacat acctcgctct gctaatcctg ttaccagtgg    4380
ctgctgccag tggcgataag tcgtgtctta ccgggttgga ctcaagacga tagttaccgg    4440
ataaggcgca gcggtcgggc tgaacggggg gttcgtgcac acagcccagc ttggagcgaa    4500
cgacctacac cgaactgaga tacctacagc gtgagcattg agaaagcgcc acgcttcccg    4560
```

-continued

| | |
|---|---|
| aagggagaaa ggcggacagg tatccggtaa gcggcagggt cggaacagga gagcgcacga | 4620 |
| gggagcttcc aggggggaac gcctggtatc tttatagtcc tgtcgggttt cgccacctct | 4680 |
| gacttgagcg tcgattttg tgatgctcgt caggggggcc gagcctatgg aaaaacgcca | 4740 |
| gcaacgcggc cttttttacgg ttcctggcct ttttgctggcc ttttgctcac atgttctttc | 4800 |
| ctgcgttatc ccctgattct gtggataacc gtattaccgc ctttgagtga gctgataccg | 4860 |
| ctcgccgcag ccgaacgacc gagcgcagcg agtcagtgag cgaggaagcg gaagagcgcc | 4920 |
| caatacgcaa accgcctctc cccgcgcgtt ggccgattca ttaatgcagc tggcacgaca | 4980 |
| ggtttcccga ctggaaagcg ggcagtgagc gcaacgcaat taatgtgagt tacctcactc | 5040 |
| attaggcacc ccaggcttta cactttatgc ttccggctcc tatgttgtgt ggaattgtga | 5100 |
| gcggataaca atttcacaca ggaaacagct atgaccatga ttacgccaag ctcggaatta | 5160 |
| accctcacta aagggaacaa aagctggcta gt | 5192 |

<210> SEQ ID NO 3
<211> LENGTH: 74
<212> TYPE: DNA
<213> ORGANISM: Artificial Sequence
<220> FEATURE:
<223> OTHER INFORMATION: Primer

<400> SEQUENCE: 3

| | |
|---|---|
| gcaagcggag gtggtggatc tggaggtgga ggttctggag gtggtggatc tcaggtccag | 60 |
| ctggtgcagt ctgg | 74 |

<210> SEQ ID NO 4
<211> LENGTH: 69
<212> TYPE: DNA
<213> ORGANISM: Artificial Sequence
<220> FEATURE:
<223> OTHER INFORMATION: Primer

<400> SEQUENCE: 4

| | |
|---|---|
| ttggaggagg gtgccagggg gaagaccgat gggcccttgg tactagctga ggagacggtg | 60 |
| accagggtg | 69 |

<210> SEQ ID NO 5
<211> LENGTH: 74
<212> TYPE: DNA
<213> ORGANISM: Artificial Sequence
<220> FEATURE:
<223> OTHER INFORMATION: Primer

<400> SEQUENCE: 5

| | |
|---|---|
| gcaagcggag gtggtggatc tggaggtgga ggttctggag gtggtggatc tcaggtcacc | 60 |
| ttgaaggagt ctgg | 74 |

<210> SEQ ID NO 6
<211> LENGTH: 74
<212> TYPE: DNA
<213> ORGANISM: Artificial Sequence
<220> FEATURE:
<223> OTHER INFORMATION: Primer

<400> SEQUENCE: 6

| | |
|---|---|
| gcaagcggag gtggtggatc tggaggtgga ggttctggag gtggtggatc tgaggtgcag | 60 |
| ctggtggagt ctgg | 74 |

<210> SEQ ID NO 7
<211> LENGTH: 71
<212> TYPE: DNA
<213> ORGANISM: Artificial Sequence
<220> FEATURE:
<223> OTHER INFORMATION: Primer

<400> SEQUENCE: 7
ttggaggagg gtgccagggg gaagaccgat gggcccttgg tactagctga agagacggtg    60
accattgtcc c                                                        71

<210> SEQ ID NO 8
<211> LENGTH: 74
<212> TYPE: DNA
<213> ORGANISM: Artificial Sequence
<220> FEATURE:
<223> OTHER INFORMATION: Primer

<400> SEQUENCE: 8
gcaagcggag gtggtggatc tggaggtgga ggttctggag gtggtggatc tcaggtgcag    60
ctgcaggagt cggg                                                     74

<210> SEQ ID NO 9
<211> LENGTH: 71
<212> TYPE: DNA
<213> ORGANISM: Artificial Sequence
<220> FEATURE:
<223> OTHER INFORMATION: Primer

<400> SEQUENCE: 9
ttggaggagg gtgccagggg gaagaccgat gggcccttgg tactagctga ggagacggtg    60
accagggttc c                                                        71

<210> SEQ ID NO 10
<211> LENGTH: 74
<212> TYPE: DNA
<213> ORGANISM: Artificial Sequence
<220> FEATURE:
<223> OTHER INFORMATION: Primer

<400> SEQUENCE: 10
gcaagcggag gtggtggatc tggaggtgga ggttctggag gtggtggatc tgaggtgcag    60
ctggtgcagt ctgg                                                     74

<210> SEQ ID NO 11
<211> LENGTH: 80
<212> TYPE: DNA
<213> ORGANISM: Artificial Sequence
<220> FEATURE:
<223> OTHER INFORMATION: Primer

<400> SEQUENCE: 11
aagatgcagt tacttcgctg tttttcaata ttttctgtta ttgctagcgt tttagcagac    60
atccagatga cccagtctcc                                               80

<210> SEQ ID NO 12
<211> LENGTH: 72
<212> TYPE: DNA
<213> ORGANISM: Artificial Sequence
<220> FEATURE:
<223> OTHER INFORMATION: Primer

<400> SEQUENCE: 12

-continued agatccacca cctccagaac ctccacctcc agatccacca cctccgcttg ctttgatttc    60
caccttggtc cc    72

```
<210> SEQ ID NO 13
<211> LENGTH: 80
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (61)..(61)
<223> OTHER INFORMATION: n = a or g
<220> FEATURE:
<221> NAME/KEY: misc_feature
<222> LOCATION: (76)..(76)
<223> OTHER INFORMATION: n = a or t
```

<400> SEQUENCE: 13
aagatgcagt tacttcgctg tttttcaata ttttctgtta ttgctagcgt tttagcagat    60
nttgtgatga ctcagnctcc    80

```
<210> SEQ ID NO 14
<211> LENGTH: 72
<212> TYPE: DNA
<213> ORGANISM: Artificial Sequence
<220> FEATURE:
<223> OTHER INFORMATION: Primer
```

<400> SEQUENCE: 14
agatccacca cctccagaac ctccacctcc agatccacca cctccgcttg ctttgatctc    60
cagcttggtc cc    72

```
<210> SEQ ID NO 15
<211> LENGTH: 80
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (67)..(67)
<223> OTHER INFORMATION: n = a or t
```

<400> SEQUENCE: 15
aagatgcagt tacttcgctg tttttcaata ttttctgtta ttgctagcgt tttagcagaa    60
attgtgntga cgcagtctcc    80

```
<210> SEQ ID NO 16
<211> LENGTH: 72
<212> TYPE: DNA
<213> ORGANISM: Artificial Sequence
<220> FEATURE:
<223> OTHER INFORMATION: Primer
```

<400> SEQUENCE: 16
agatccacca cctccagaac ctccacctcc agatccacca cctccgcttg ctttgatatc    60
cactttggtc cc    72

```
<210> SEQ ID NO 17
<211> LENGTH: 80
<212> TYPE: DNA
<213> ORGANISM: Artificial Sequence
<220> FEATURE:
<223> OTHER INFORMATION: Primer
```

```
<220> FEATURE:
<221> NAME/KEY: misc_feature
<222> LOCATION: (67)..(67)
<223> OTHER INFORMATION: n = c or t

<400> SEQUENCE: 17
aagatgcagt tacttcgctg tttttcaata ttttctgtta ttgctagcgt tttagcacag      60
tctgtgntga cgcagccgcc                                                  80

<210> SEQ ID NO 18
<211> LENGTH: 71
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (61)..(61)
<223> OTHER INFORMATION: n = c or g
<220> FEATURE:
<221> NAME/KEY: misc_feature
<222> LOCATION: (63)..(63)
<223> OTHER INFORMATION: n = c or g

<400> SEQUENCE: 18
agatccacca cctccagaac ctccacctcc agatccacca cctccgcttg ctaggacggt      60
nancttggtc c                                                           71

<210> SEQ ID NO 19
<211> LENGTH: 78
<212> TYPE: DNA
<213> ORGANISM: Artificial Sequence
<220> FEATURE:
<223> OTHER INFORMATION: Primer

<400> SEQUENCE: 19
aagatgcagt tacttcgctg tttttcaata ttttctgtta ttgctagcgt tttagcacag      60
tctgccctga ctcagcct                                                    78

<210> SEQ ID NO 20
<211> LENGTH: 79
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (65)..(65)
<223> OTHER INFORMATION: n = a or t
<220> FEATURE:
<221> NAME/KEY: misc_feature
<222> LOCATION: (72)..(72)
<223> OTHER INFORMATION: n = a or t

<400> SEQUENCE: 20
aagatgcagt tacttcgctg tttttcaata ttttctgtta ttgctagcgt tttagcatcc      60
tatgngctga cncagccac                                                   79
```